(12) United States Patent
McDermott

(10) Patent No.: US 12,653,540 B2
(45) Date of Patent: Jun. 16, 2026

(54) DEVICES, ASSEMBLIES, AND METHODS FOR DELIVERING AGENTS

(71) Applicant: Boston Scientific Scimed, Inc., Maple Grove, MN (US)

(72) Inventor: Adam Gregory McDermott, Lincoln, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 392 days.

(21) Appl. No.: 18/351,584

(22) Filed: Jul. 13, 2023

(65) Prior Publication Data

US 2024/0016501 A1 Jan. 18, 2024

Related U.S. Application Data

(60) Provisional application No. 63/368,425, filed on Jul. 14, 2022.

(51) Int. Cl.
*A61B 17/12* (2006.01)
*A61M 39/22* (2006.01)

(52) U.S. Cl.
CPC ....... *A61B 17/12186* (2013.01); *A61M 39/22* (2013.01)

(58) Field of Classification Search
CPC ........ A61B 17/00491; A61B 17/12186; A61B 2017/00292; A61B 2017/00367;
(Continued)

(56) References Cited

U.S. PATENT DOCUMENTS 471,854 A 3/1892 Howard
881,238 A 3/1908 Hasbrouck
(Continued)

FOREIGN PATENT DOCUMENTS

CN 101401956 B 11/2012
DE 60215438 T2 8/2007
(Continued)

OTHER PUBLICATIONS

International Search Report and Written Opinion issued in International Application No. PCT/US2023/070096, issued Oct. 12, 2023 (14 pages).
(Continued)

*Primary Examiner* — Robert A Lynch
(74) *Attorney, Agent, or Firm* — Bookoff McAndrews, PLLC

(57) ABSTRACT

A valve assembly for a medical device that includes a piston configured to move relative to an enclosure of the medical device, the enclosure including a first region in fluid communication with an agent, and a second region in fluid communication with a source of fluid. The piston includes a chamber disposed on a sidewall of the piston which is configured to receive the agent. The piston is configured to move to a first position where the chamber is in fluid communication with the first region and not in fluid communication with the second region such that the agent is received within the chamber, and further configured to move to a second position where the chamber is in fluid communication with the second region and not in fluid communication with the first region, such that the agent within the chamber is mixed with the fluid received in the second region.

20 Claims, 6 Drawing Sheets

(58) Field of Classification Search
CPC .......... A61B 2017/00491; A61B 2017/00495;
A61B 2017/00522; A61B 2017/00544;
A61M 39/22; A61M 2039/224; A61M
2039/2486; A61M 11/02; A61M 11/06;
A61M 11/003; A61M 13/00; A61M
31/00; A61M 15/0005; A61M 15/0065;
A61M 2205/073; A61M 2205/106; A61M
5/19; A61M 5/2448; A61M 5/284; A61M
5/30; A61M 5/3129; A61M 5/31596
See application file for complete search history.

(56) References Cited

U.S. PATENT DOCUMENTS

| | | | |
|---|---|---|---|
| 1,145,520 A | 7/1915 | Smith | |
| 1,599,959 A | 9/1926 | Buheiji | |
| 1,732,566 A | 10/1929 | McKendrick | |
| 2,151,418 A | 3/1939 | Bolté | |
| 2,185,927 A | 1/1940 | Shelanski | |
| 2,478,715 A | 8/1949 | Schmitt | |
| 2,623,519 A | 12/1952 | Cohen | |
| 3,669,113 A | 6/1972 | Altounyan et al. | |
| 3,940,061 A | 2/1976 | Gimple et al. | |
| 4,184,258 A | 1/1980 | Barrington et al. | |
| 4,427,450 A | 1/1984 | Kostansek | |
| 4,457,329 A | 7/1984 | Werley et al. | |
| 4,806,167 A | 2/1989 | Raythatha | |
| 5,215,221 A | 6/1993 | Dirksing | |
| 5,231,983 A | 8/1993 | Matson et al. | |
| 5,273,531 A | 12/1993 | Knoepfler | |
| 5,312,331 A | 5/1994 | Kneopfler | |
| 5,312,333 A | 5/1994 | Churinetz et al. | |
| 5,366,122 A | 11/1994 | Guentert et al. | |
| 5,445,612 A | 8/1995 | Terakura et al. | |
| 5,470,311 A | 11/1995 | Setterstrom et al. | |
| 5,617,845 A | 4/1997 | Poss et al. | |
| 5,857,457 A | 1/1999 | Hyppola | |
| 5,884,621 A | 3/1999 | Matsugi et al. | |
| 5,951,531 A | 9/1999 | Ferdman et al. | |
| 6,003,512 A | 12/1999 | Gerde | |
| 6,484,750 B1 | 11/2002 | Foos et al. | |
| 6,554,022 B2 | 4/2003 | Wakeman | |
| 6,589,087 B2 | 7/2003 | Mackal et al. | |
| 6,684,917 B2 | 2/2004 | Zhu et al. | |
| 6,708,712 B2 | 3/2004 | Wakeman | |
| 6,716,190 B1 | 4/2004 | Glines et al. | |
| 6,799,571 B1 | 10/2004 | Hughes et al. | |
| 7,178,547 B2 | 2/2007 | Mackal | |
| 7,311,270 B2 | 12/2007 | Kapila | |
| 7,334,598 B1 | 2/2008 | Hollars | |
| 7,361,300 B2 | 4/2008 | Kelly et al. | |
| 7,427,607 B2 | 9/2008 | Suzuki | |
| 7,455,248 B2 | 11/2008 | Kablik et al. | |
| 7,461,649 B2 | 12/2008 | Gamard et al. | |
| 7,544,177 B2 | 6/2009 | Gertner | |
| 7,563,299 B2 | 7/2009 | Baptista da Costa et al. | |
| 7,673,647 B2 | 3/2010 | Mackal | |
| 7,841,338 B2 | 11/2010 | Dunne et al. | |
| 7,892,205 B2 | 2/2011 | Palasis et al. | |
| 7,921,874 B2 | 4/2011 | Tekulve et al. | |
| 8,037,880 B2 | 10/2011 | Zhu et al. | |
| 8,097,071 B2 | 1/2012 | Burgess et al. | |
| 8,118,777 B2 | 2/2012 | Ducharme et al. | |
| 8,269,058 B2 | 9/2012 | McCarthy et al. | |
| 8,313,474 B2 | 11/2012 | Campbell et al. | |
| 8,360,276 B2 | 1/2013 | Rogier et al. | |
| 8,361,054 B2 | 1/2013 | Ducharme et al. | |
| 8,496,189 B2 | 7/2013 | Lomond et al. | |
| 8,673,065 B2 | 3/2014 | Burgess et al. | |
| 8,721,582 B2 | 5/2014 | Ji | |
| 8,741,335 B2 | 6/2014 | McCarthy | |
| 8,827,980 B2 | 9/2014 | Ji | |
| 8,910,627 B2 | 12/2014 | Iwatschenko et al. | |
| 8,951,565 B2 | 2/2015 | McCarthy | |
| 9,028,437 B2 | 5/2015 | Ott et al. | |
| 9,089,658 B2 | 7/2015 | Dunne et al. | |
| 9,101,744 B2 | 8/2015 | Ducharme | |
| 9,107,668 B2 | 8/2015 | Melsheimer et al. | |
| 9,132,206 B2 | 9/2015 | McCarthy | |
| 9,204,957 B2 | 12/2015 | Gregory et al. | |
| 9,205,170 B2 | 12/2015 | Lucchesi et al. | |
| 9,205,207 B2 | 12/2015 | Ji | |
| 9,205,240 B2 | 12/2015 | Greenhalgh et al. | |
| 9,308,584 B2 | 4/2016 | Burgess et al. | |
| 9,310,812 B2 | 4/2016 | Costle et al. | |
| 9,375,533 B2 | 6/2016 | Ducharme et al. | |
| 9,492,646 B2 | 11/2016 | Hoogenakker et al. | |
| 9,517,976 B2 | 12/2016 | Mackal | |
| 9,545,490 B2 | 1/2017 | Iwatschenko et al. | |
| 9,555,185 B2 | 1/2017 | Foster et al. | |
| 9,629,966 B2 | 4/2017 | Ji | |
| 9,636,470 B2 | 5/2017 | Pohlmann et al. | |
| 9,707,359 B2 | 7/2017 | Kubo | |
| 9,713,682 B2 | 7/2017 | Eistetter et al. | |
| 9,717,897 B2 | 8/2017 | Rogier | |
| 9,821,084 B2 | 11/2017 | Diegelmann et al. | |
| 9,839,772 B2 | 12/2017 | Ducharme | |
| 9,839,774 B2 | 12/2017 | Bonaldo | |
| 9,846,439 B2 | 12/2017 | Carman et al. | |
| 9,867,931 B2 | 1/2018 | Gittard | |
| 9,976,660 B2 | 5/2018 | Stanton et al. | |
| 10,004,690 B2 | 6/2018 | Lee et al. | |
| 10,010,705 B2 | 7/2018 | Greenhalgh et al. | |
| 10,017,231 B2 | 7/2018 | Fawcett, Jr. | |
| 10,036,617 B2 | 7/2018 | Mackal | |
| 10,065,004 B2 | 9/2018 | Eder et al. | |
| 10,173,019 B2 | 1/2019 | Kaufmann et al. | |
| 10,384,049 B2 | 8/2019 | Stanton et al. | |
| 10,463,811 B2 | 11/2019 | Lee et al. | |
| 10,507,293 B2 | 12/2019 | Goodman et al. | |
| 10,646,706 B2 | 5/2020 | Rogier | |
| 10,730,595 B2 | 8/2020 | Fawcett | |
| 10,751,523 B2 | 8/2020 | Rogier | |
| 10,806,853 B2 | 10/2020 | Gittard | |
| 10,850,814 B2 | 12/2020 | Fawcett | |
| 10,994,818 B2 | 5/2021 | Hernandez | |
| 2004/0107963 A1 | 6/2004 | Finlay et al. | |
| 2004/0249359 A1 | 12/2004 | Palasis et al. | |
| 2005/0121025 A1 | 6/2005 | Gamard et al. | |
| 2005/0147656 A1 | 7/2005 | McCarthy et al. | |
| 2005/0220721 A1 | 10/2005 | Kablik et al. | |
| 2006/0004314 A1 | 1/2006 | McCarthy et al. | |
| 2006/0213514 A1 | 9/2006 | Price et al. | |
| 2007/0056586 A1 | 3/2007 | Price et al. | |
| 2007/0066920 A1 | 3/2007 | Hopman et al. | |
| 2007/0066924 A1 | 3/2007 | Hopman et al. | |
| 2007/0082023 A1 | 4/2007 | Hopman et al. | |
| 2007/0083137 A1 | 4/2007 | Hopman et al. | |
| 2007/0125375 A1 | 6/2007 | Finlay et al. | |
| 2007/0151560 A1 | 7/2007 | Price et al. | |
| 2007/0199824 A1 | 8/2007 | Hoerr et al. | |
| 2008/0021374 A1 | 1/2008 | Kawata | |
| 2008/0287907 A1 | 11/2008 | Gregory et al. | |
| 2009/0101144 A1 | 4/2009 | Gamard et al. | |
| 2009/0155342 A1 | 6/2009 | Diegemann et al. | |
| 2009/0260626 A1 | 10/2009 | Von Schuckmann | |
| 2009/0281486 A1 | 11/2009 | Ducharme | |
| 2010/0121261 A1 | 5/2010 | Kablik et al. | |
| 2010/0305505 A1 | 12/2010 | Ducharme et al. | |
| 2011/0073200 A1 | 3/2011 | Overvaag et al. | |
| 2011/0274726 A1 | 11/2011 | Guo et al. | |
| 2011/0308516 A1 | 12/2011 | Price et al. | |
| 2014/0203098 A1 | 7/2014 | Bierie | |
| 2014/0271491 A1 | 9/2014 | Gittard et al. | |
| 2015/0094649 A1 | 4/2015 | Gittard | |
| 2015/0125513 A1 | 5/2015 | McCarthy | |
| 2017/0106181 A1 | 4/2017 | Bonaldo et al. | |
| 2017/0232141 A1 | 8/2017 | Surti et al. | |
| 2017/0252479 A1 | 9/2017 | Ji et al. | |
| 2017/0296760 A1 | 10/2017 | Lee et al. | |
| 2018/0099088 A1 | 4/2018 | Gittard | |
| 2018/0193574 A1 | 7/2018 | Smith et al. | |
| 2018/0214160 A1 | 8/2018 | Hoskins et al. | |
| 2018/0339144 A1 | 11/2018 | Greenhalgh et al. | |

(56) References Cited

U.S. PATENT DOCUMENTS

| | | |
|---|---|---|
| 2019/0134366 A1 | 5/2019 | Erez et al. |
| 2019/0217315 A1 | 7/2019 | Maguire et al. |
| 2019/0232030 A1 | 8/2019 | Pic et al. |
| 2020/0100986 A1 | 4/2020 | Pic et al. |
| 2021/0024187 A1 | 1/2021 | Fawcett et al. |
| 2021/0069485 A1 | 3/2021 | Rogier |
| 2021/0205543 A1 | 7/2021 | Pic et al. |
| 2021/0275157 A1 | 9/2021 | Pic et al. |

FOREIGN PATENT DOCUMENTS

| | | | |
|---|---|---|---|
| DE | 10 2007 017724 A1 | 10/2008 | |
| DE | 101 65 101 B3 | 2/2014 | |
| EP | 3052168 B1 | 11/2019 | |
| JP | H07118305 A | 5/1995 | |
| WO | WO-9303782 A1 * | 3/1993 | ........ A61M 15/0068 |
| WO | 03013552 A1 | 2/2003 | |
| WO | 2004066806 A2 | 8/2004 | |
| WO | 2005062896 A2 | 7/2005 | |
| WO | 2006071649 A2 | 7/2006 | |
| WO | 2006088912 A2 | 8/2006 | |
| WO | 2008033462 A2 | 3/2008 | |
| WO | 2009061409 A1 | 5/2009 | |
| WO | 2015050814 A1 | 4/2015 | |
| WO | 2018157772 A1 | 9/2018 | |
| WO | 2021/0178853 A1 | 9/2021 | |

OTHER PUBLICATIONS

Bridevaux, Pierre-Olivier, et al. "Short-term safety of thoracoscopic talc pleurodesis for recurrent primary spontaneous pneumothorax: a prospective European multicentre study." European Respiratory Journal 38.4 (2011): 770-773.
Giday, Samuel, et al. "Safety analysis of a hemostatic powder in a porcine model of acute severe gastric bleeding." Digestive diseases and sciences 58.12 (2013): 3422-3428.
Giday, Samuel A., et al. "A long-term randomized controlled trial of a novel nanopowder hemostatic agent for control of severe upper gastrointestinal bleeding in a porcine model." Gastrointestinal Endoscopy 69.5 (2009): AB133.
Giday, S. A., et al. "Long-term randomized controlled trial of a novel nanopowder hemostatic agent (TC-325) for control of severe arterial upper gastrointestinal bleeding in a porcine model." Endoscopy 43.04 (2011): 296-299.
Regalia, Kristen, et al. "Hemospray in Gastrointestinal Bleeding." Practical Gastroenterology. Endoscopy: Opening New Eyes, ser. 8, May 2014, pp. 13-24. 8.
Cook Medical. Hemospray Endoscopic Hemostat, Cook, 2014. (7 pages, in English).
"Hemospray Clinical Experience Shows Efficacy of a New Hemostasis Modality—v1", Cook Medical, 2012.
"Hemospray Clinical Experience Shows Efficacy of a New Hemostasis Modality—v2", Cook Medical, 2013.
"Hemospray Clinical Experience Shows Efficacy of a New Hemostasis Modality—v3", Cook Medical, 2014.
Aslanian, Harry R., and Loren Laine. "Hemostatic powder spray for GI bleeding." Gastrointestinal endoscopy 77.3 (2013): 508-510.
Giday, S. A., et al. "Long-term randomized controlled trial of a novel nanopowder hemostatic agent (TC-325) for control of severe arterial upper gastrointestinal bleeding in a porcine model." Endoscopy 43.04 (2011): 296-299. via ResearchGate.
RETSCH GmbH Haan. Sieve Analysis: Taking a Close Look at Quality, An Expert Guide to Particle Size Analysis. 2015. (56 pages, in English).
Micromeritics. Density Analysis, 2001. (6 pages, in English).
Micromeritics. "Application Note: Bulk and Skeletal Density Computations for the AutoPore." May 2012. (3 pages, in English).
Arefnia, Ali, et al. "Comparative Study on the Effect of Tire-Derived Aggregate on Specific Gravity of Kaolin." Electronic Journal of Geotechnical Engineering 18 (2013): 335-44.
Kesavan, Jana, et al. "Density Measurements of Materials Used in Aerosol Studies". Edgewood Chemical Biological Center Aberdeen Proving Ground MD, 2000.

* cited by examiner

DEVICES, ASSEMBLIES, AND METHODS FOR DELIVERING AGENTS

CROSS-REFERENCE TO RELATED APPLICATIONS

This application claims the benefit of priority of U.S. Provisional Patent Application No. 63/368,425, filed on Jul. 14, 2022, the entirety of which is incorporated herein by reference.

TECHNICAL FIELD

Various aspects of this disclosure relate generally to devices and methods for delivering agents. More specifically, in embodiments, this disclosure relates to devices for delivery of powdered agents, such as hemostatic agents.

BACKGROUND

In certain medical procedures, it may be necessary to minimize or stop bleeding internal to the body. For example, an endoscopic medical procedure may require hemostasis of bleeding tissue within the gastrointestinal tract, for example in the esophagus, stomach, or intestines. During an endoscopic procedure, a user inserts a sheath of an endoscope into a body lumen of a patient. The user utilizes a handle of the endoscope to control the endoscope during the procedure. Tools may be passed through a working channel of the endoscope via, for example, a port in the handle, to deliver treatment at the procedure site near a distal end of the endoscope. The procedure site is remote from the user.

To achieve hemostasis at the remote site, a hemostatic agent may be delivered by a device inserted into the working channel of the endoscope. Agent delivery may be achieved, for example, through mechanical systems. Such systems, however, may require numerous steps or actuations to achieve delivery, may not achieve a desired rate of agent delivery or a desired dosage of agent, may result in the agent clogging portions of the delivery device, may result in inconsistent dosing of the agent, and/or may not result in the agent reaching the treatment site deep within the gastrointestinal tract. The current disclosure may solve one or more of these issues or other issues in the art.

SUMMARY

Each of the aspects disclosed herein may include one or more of the features described in connection with any of the other disclosed aspects.

Aspects of the disclosure relate to, among other things, systems, devices, and methods for delivering an agent to a target treatment site using a medical device including a valve assembly. According to an example, a valve assembly for a medical device may include a piston configured to move relative to an enclosure of the medical device, the enclosure including a first region that is in fluid communication with an agent, and a second region that is in fluid communication with a source of fluid, the piston including a chamber disposed on a sidewall of the piston, wherein the chamber is configured to receive the agent, wherein the piston is configured to move to a first position relative to the enclosure with the chamber in fluid communication with the first region and not in fluid communication with the second region, such that the agent is received within the chamber, and wherein the piston is configured to move to a second position relative to the enclosure with the chamber in fluid communication with the second region and not in fluid communication with the first region, such that the agent received in the chamber is mixed with the fluid received in the second region, thereby controlling delivery of the agent and the fluid from the medical device.

Any of the valve assemblies described herein may include any of the following features. The chamber comprises a closed cavity within the sidewall of the piston. The closed cavity has a hemispherical-shape. The piston is configured to move to a third position relative to the enclosure, wherein in the third position, the piston is transitioned to an intermediary region disposed between the first region and the second region, and wherein the intermediary region is not in fluid communication with either of the first region or the second region. The intermediary region is configured to seal the chamber when the shaft is in the third position. The piston is coupled to an actuation mechanism of the medical device, the actuation mechanism is configured to move the piston relative to the enclosure for delivering the agent from the first region to the second region. The actuation mechanism comprises a pneumatic system, the pneumatic system comprising a piston rod and a spring. A proximal end of the piston is coupled to the piston rod. The piston is configured to be biased to the first position with the chamber received within the first region. The chamber is sized to define a volume that corresponds to a predetermined volume of the agent. The enclosure includes a funnel positioned within the second region, and the piston is configured to release the agent onto an interior surface of the funnel when in the second position. The funnel is in fluid communication with the source of fluid, and the funnel is porous such that the fluid received in the second region passes through the funnel for mixing with the agent. The funnel is configured to deliver the agent and the fluid to a delivery conduit of the medical device that is in fluid communication with the second region when the agent and the fluid are mixed along the funnel. The valve assembly includes an outlet coupled to the second region. The valve assembly includes a catheter coupled to the outlet, wherein the agent is released into the catheter via the outlet.

According to another example, a device for delivering an agent includes a pressurized fluid source configured to store a pressurized fluid; an enclosure configured to store the agent, the enclosure including an inlet region in fluid communication with the agent and an outlet region in fluid communication with the pressurized fluid source; and a valving assembly disposed within the enclosure, the valving assembly including piston shaft having a chamber disposed along a sidewall of the piston, wherein the piston is configured to move between a first position and a second position relative to the enclosure to selectively guide the agent from the inlet region to the outlet region; wherein, in the first position, the chamber is positioned within the inlet region such that the shaft is configured to receive the agent in the chamber; and wherein, in the second position, the chamber is positioned within the outlet region such that the shaft is configured to release the agent from the chamber to mix with the pressurized fluid received from the pressurized fluid source.

Any of the devices disclosed herein may include any of the following features. The piston is configured to move to a third position relative to the enclosure; wherein, in the first position, the piston is fully disposed within the inlet region such that the chamber is in fluid communication with the inlet region, wherein, in the third position, the piston is positioned within an intermediary region disposed between the inlet region and the outlet region such that the chamber is not in fluid communication with the agent in the inlet region and the pressurized fluid in the outlet region; and wherein, in the second position, the piston is positioned within the outlet region such that the chamber is in fluid communication with the outlet region. The chamber is configured to receive a volume of the agent when the piston is in the first position. The chamber is configured to release the volume of the agent when the piston is in the second position.

According to a further example, a method of delivering an agent from a medical device includes moving a piston to a first region of an enclosure of the medical device, the first region is in fluid communication with a source of the agent such that a chamber disposed on a sidewall of the piston receives a volume of the agent when the piston is in the first region; moving the piston to a second region of the enclosure, thereby releasing the volume of the agent received in the chamber into the second region, wherein the second region is in fluid communication with a source of fluid; releasing fluid into the second region from the source of fluid, thereby mixing the volume of the agent with the fluid within the second region; and delivering a mixture of the volume of the agent and the fluid from the second region through an outlet of the medical device that is in fluid communication with the second region.

It may be understood that both the foregoing general description and the following detailed description are exemplary and explanatory only and are not restrictive of the invention, as claimed. As used herein, the terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "diameter" may refer to a width where an element is not circular. The term "top" refers to a direction or side of a device relative to its orientation during use, and the term "bottom" refers to a direction or side of a device relative to its orientation during use that is opposite of the "top." The term "exemplary" is used in the sense of "example," rather than "ideal." The term "approximately," or like terms (e.g., "substantially"), includes values+/–10% of a stated value.

BRIEF DESCRIPTION OF THE DRAWINGS

The accompanying drawings, which are incorporated in and constitute a part of this specification, illustrate aspects of this disclosure and together with the description, serve to explain the principles of the disclosure.

DETAILED DESCRIPTION

Embodiments of this disclosure relate to dispensing devices having valve assemblies for selectively releasing an agent (e.g., a powdered agent) to a site of a medical procedure. The valve assembly may include a movable piston for moving the agent from a first area that stores the agent, the first area not being in fluid communication with a pressurized medium source (e.g., a gas canister), to a second area in which the agent encounters the pressurized fluid (e.g., a gas). The agent may be received within an enclosure of the dispensing device, and in fluid communication with the pressurized fluid through an outlet of the valve assembly. Accordingly, when the agent is selectively moved into fluid communication with the pressurized fluid source by the movable piston of the valve assembly, the agent may be agitated by the fluid prior to delivery to a target site of the medical procedure. Aspects of the dispensing device and valve assembly, such as the movable piston, may facilitate a controlled fluidization of the agent with the flow of pressurized fluid prior to the agent being delivered, which may assist in selectively controlling the flow of agent out of the dispensing device to help to prevent or minimize clogging during delivery.

Figure 1:
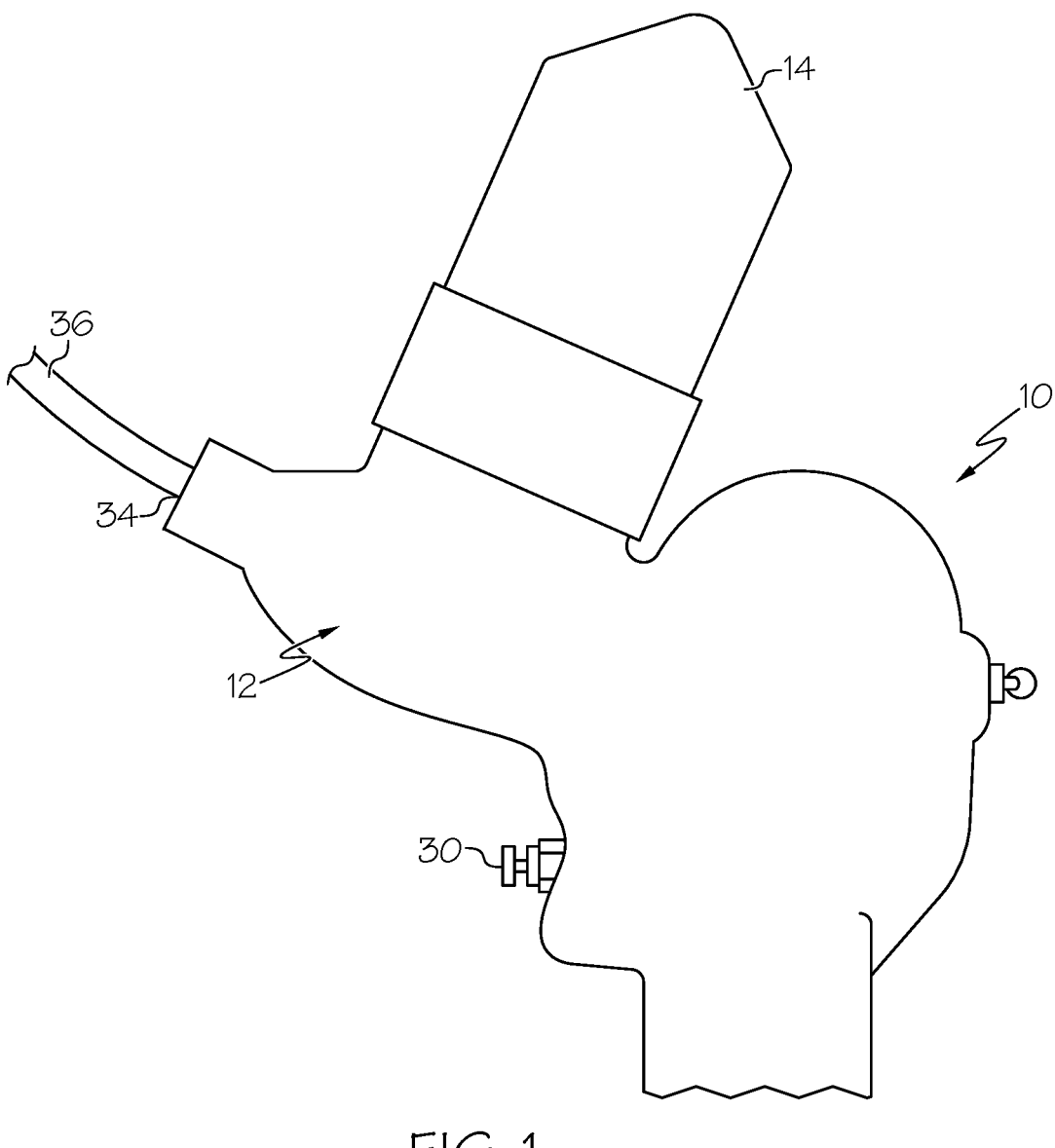
FIG. 1 shows an exemplary delivery device according to some embodiments.

FIG. 1 shows a delivery system 10, which may be a powder delivery system. Delivery system 10 may include a handle body 12. Handle body 12 may include, or may be configured to receive, an enclosure 14 (or other source or container) storing a material (e.g., a powdered agent). Enclosure 14 may be coupled to handle body 12 for providing the agent to handle body 12, or a lid/enclosure of the agent may be screwed onto, or otherwise coupled to, enclosure 14 for supplying the agent to enclosure 14. The agent may be, for example, a powdered agent, such as a hemostatic agent. The agent may alternatively be another type of agent or material, or form of agent (e.g., a liquid or gel agent), and may have any desired function. Enclosure 14 may be removably attached to other components of delivery system 10, including components of handle body 12.

Handle body 12 may have a variety of features, to be discussed in further detail herein. U.S. patent application Ser. No. 16/589,633, filed Oct. 1, 2019, published as U.S. Patent Application Publication No. 2020/0100986 A1 on Apr. 2, 2022, the disclosure of which is hereby incorporated by reference in its entirety, discloses features of exemplary delivery devices and systems. The features of this disclosure may be combined with any of the features described in the above-referenced application. The features described herein may be used alone or in combination and are not mutually exclusive. Like reference numbers and/or terminology are used to denote similar structures, when possible.

Still referring to FIG. 1, delivery system 10 may include an actuation mechanism 30 used to activate flow of a pressurized fluid (e.g., gas) from a pressurized medium source in fluid communication with delivery system 10. Actuation mechanism 30 may be selectively actuated (e.g., manually depressible) or otherwise moved or actuated to control delivery of a material (e.g., a powdered agent) and pressurized fluid. The pressurized fluid alone, or a combination of a powdered agent and fluid, may be delivered from an outlet 34 of handle body 12. Outlet 34 may be in fluid communication with a delivery conduit, for example catheter 36 or another component for delivering the combination of agent and fluid to a desired location within a body lumen of a patient.

Figure 2:
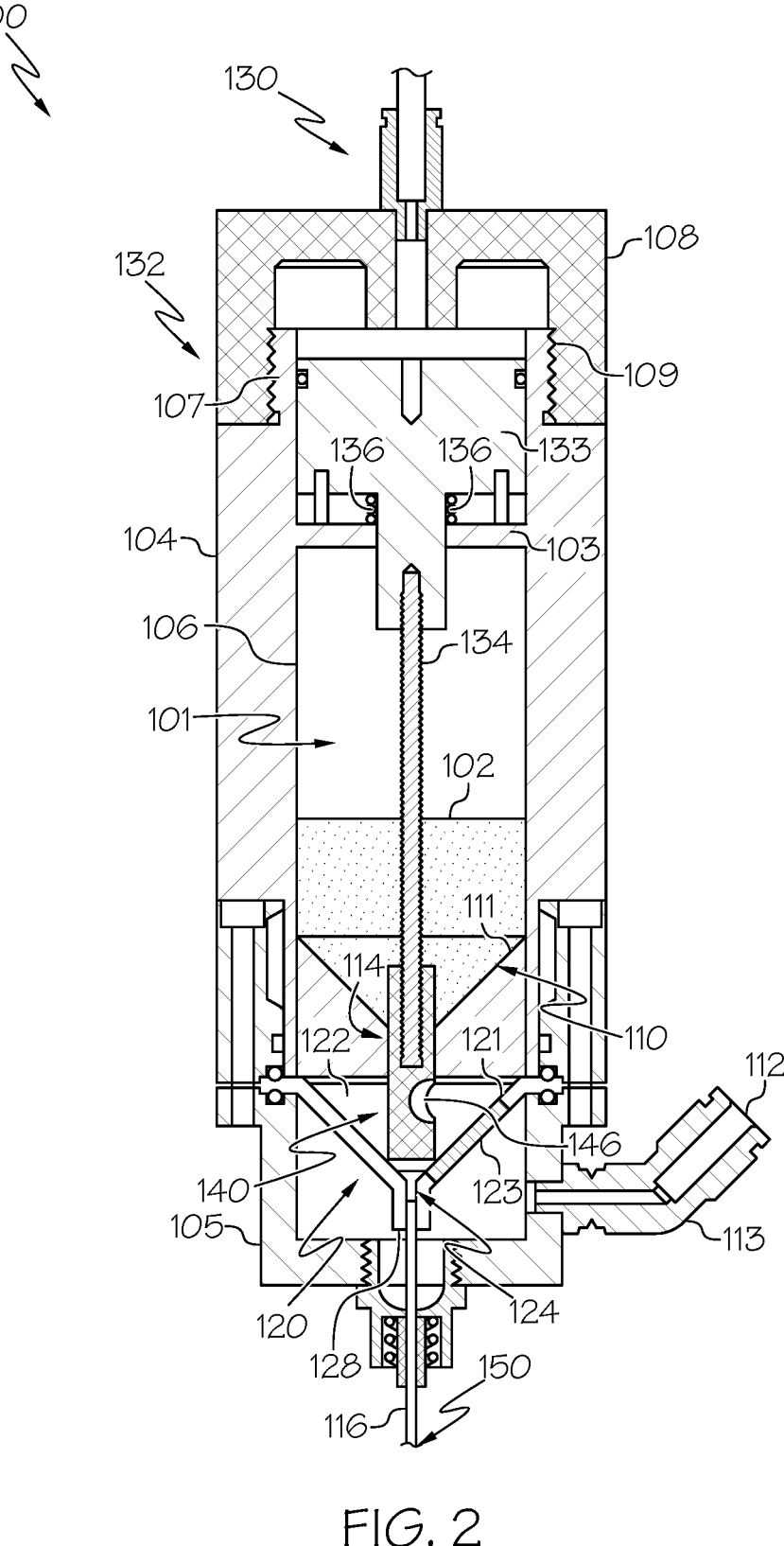
FIG. 2 shows a cross-sectional view of a valve assembly of the delivery device of FIG. 1 according to some embodiments.

FIG. 2 shows aspects of an exemplary valve assembly 100. Valve assembly 100 may be housed within handle body 12 of delivery system 10, and selectively actuated by actuation mechanism 30. Actuation mechanism 30 may be coupled to valve assembly 100 by a mechanical connection 130. For example, mechanical connection 130 may include a cable, a wire, a rod, or various other suitable mechanisms for connecting one or more internal components of valve assembly 100 to actuation mechanism 30. Although not shown, actuation mechanism 30 may include one or more other actuation elements, such as, for example, a trigger, a button, a slider, a lever, a knob, a dial, and various other suitable actuators. As described herein, actuation of actuation mechanism 30 may provide for a corresponding movement of valve assembly 100, and particularly mechanical connection 130, thereby controlling a delivery of pressurized fluid and agent through valve assembly 100.

Valve assembly 100 may include an enclosure 104, which may be configured to store an agent, for example agent 102 (e.g. a powder). As shown in FIG. 2, for example, enclosure 104 may include a cavity 101 that is be defined by inner surfaces of a housing 106. Enclosure 104 may be coupled to a cap and/or cover at opposing ends, such as a lower cap 105 at a distal (lower) end of housing 106 and an upper lid 108 at a proximal (upper) end of housing 106. Each of enclosure 104 and upper lid 108 may include complementary threaded portions enabling a distal end of lid 108 (e.g., a lower end) to be coupled onto a proximal end of enclosure 104 (e.g., an upper end). For example, an outer surface of enclosure 104 may include a threaded portion 109 at the proximal end, and an inner surface of lid 108 may include a corresponding threaded portion 107 at the distal end for engaging threaded portion 109. It should be understood that enclosure 104 and lower cap 105 may similarly include complementary engagement mechanisms for coupling lower cap 105 to the distal (lower) end of housing 106.

In some embodiments, lower cap 105 may include a fluid inlet 112 that is in fluid communication with a pressurized medium source, such that valve assembly 100 may be configured to receive the pressurized fluid within lower cap 105 via fluid inlet 112. A wall of fluid inlet 112 may include an interface and/or protrusion 113. For example, protrusion 113 may include a lip and/or other interface for facilitating a connection between fluid inlet 112 and a tubing for delivering fluid into valve assembly 100 at lower cap 105. Although fluid inlet 112 is shown along a sidewall of lower cap 105, it will be appreciated that fluid inlet 112 may be positioned in various alternative locations relative to valve assembly 100. For example, fluid inlet 112 may be positioned alongside a surface of housing 106 and/or of lid 108.

Still referring to FIG. 2, valve assembly 100 may include an outlet 150 that is in fluid communication with housing 106 via lower cap 105. In some embodiments, outlet 150 may include a tubing 116 (e.g., a hypotube) that is in fluid communication with a catheter, such as, for example, catheter 36 (see FIG. 1). Outlet 150 may be in fluid communication with catheter 36 via outlet 34 of delivery system 10. As described herein, valve assembly 100 may be configured to deliver a mixture of the pressurized fluid and agent to a patient via outlet 150 and catheter 36.

Enclosure 104 may include a first (upper) funnel 110 and a second (lower) funnel 120. For example, first funnel 110 may be disposed within a distal end of enclosure 104, and second funnel 120 may be disposed within lower cap 105. First funnel 110 may be in fluid communication with a first (inlet) region of valve assembly 100, such as, for example, cavity 101. Agent 102 may be stored within cavity 101, and positioned along a wall 111 of first funnel 110. Wall 111 may have a generally conical shape, and wall 111 may terminate at a track 114 (e.g., a center opening) of first funnel 110. Wall 111 and housing 106 may collectively form an interior boundary (the first (inlet) region) for storing agent 102 within enclosure 104 prior to delivery.

In some embodiments, wall 111 may be shaped to form a varying cross-sectional profile between a proximal end and a distal end of first funnel 110. Accordingly, as agent 102 moves distally through first funnel 110, agent 102 may encounter portions of first funnel 110 that vary in size, which may assist in reducing a clogging of agent 102 within first funnel 110. Agent 102 may be prone to bridging, which may result in clogging absent the variations in size of first funnel 110. Stated differently, first funnel 110 may be configured to inhibit a packing and/or clogging of agent 102 within enclosure 104 by guiding agent 102 along wall 111 and toward track 114. As described herein, track 114 may be sized, shaped, and otherwise configured to receive a movable piston 140 of valve assembly 100 for controlling the delivery of agent 102 from first funnel 110 to second funnel 120.

Still referring to FIG. 2, second funnel 120 may include a wall 121 that has a generally conical shape. An inner surface of wall 121 may define a second (outlet) region of valve assembly 100, such as, for example, a channel 122 that terminates at a center opening 124 of second funnel 120. In some embodiments, wall 121 may be shaped such that channel 122 has a varying cross-sectional profile between a proximal end and a distal end of channel 122. As agent 102 moves distally through second funnel 120, agent 102 may encounter portions of channel 122 that vary in size, which may assist in reducing a clogging of agent 102 within channel 122. Agent 102 may be prone to bridging, which may result in clogging absent the variations in diameter of channel 122. As described in detail herein, agent 102 may be at least partially received within channel 122 in response to a corresponding movement of one or more components of valve assembly 100 (e.g., movable piston 140).

As described above, each of first funnel 110 and second funnel 120 may be substantially conical or funnel-shaped to reduce packing and/or clogging of agent 102 received therein, respectively. For example, at a proximal end of second funnel 120 (e.g., the top portion of second funnel 120), channel 122 may have a greater diameter relative to a distal end of second funnel 120 (e.g., the bottom portion of second funnel 120). Wall 121 may be angled and/or tapered such that channel 122 may define a smaller cavity in a distal direction adjacent to center opening 124. Although first funnel 110 and second funnel 120 are shown and described herein as having substantially similar shapes and/or cross-sectional profiles, it should be appreciated that each funnel may have a varying shape and/or size relative to one another without departing from a scope of this disclosure.

A proximal end of second funnel 120 may be coupled to housing 106 and positioned relatively under first funnel 110. As described further herein, movable piston 140 may move between first funnel 110 and second funnel 120 via track 144, such that the agent 102 received in first funnel 110 may be guided toward second funnel 120 by movable piston 140 moving via track 114 from a first position within first funnel 110 to a second position within second funnel 120. In the example, a proximal (top) end of wall 121 may be configured to form a seal a distal (bottom) end of housing 106. In some examples, valve assembly 100 may include one or more sealing mechanisms (e.g., O-rings) positioned between the interface of wall 121 and housing 106 to fluidly couple second funnel 120 to first funnel 110. With second funnel 120 sealed to housing 106, agent 102 and/or fluid may not exit enclosure 104, such as between an outer surface of wall 121 (at a proximal end of second funnel 120) and an inner surface of housing 106 (at a distal end of first funnel 110). Second funnel 120 may include a distal end 128 that is coupled to tubing 116, and distal end 128 may form a seal with one or more of lower cap 105 and/or housing 106. For example, distal end 128 may be sealed with respect to an inner surface of a distal wall of lower cap 105 and/or housing 106, thereby guiding a fluid and/or agent received within second funnel 120 into tubing 116.

Still referring to FIG. 2, wall 121 may have a constant thickness between a proximal and distal end of second funnel 120. In other embodiments, wall 121 may have a varying thickness. In some embodiments, at least a portion of wall 121 may be sintered and/or porous, such that portion of wall 121 may include a plurality of pores and/or passages 123 formed between an outer surface of wall 121 and an inner surface of wall 121 for receiving the pressurized fluid therethrough. In this instance, the plurality of passages 123 may be only positioned along the porous portion of wall 121, and the porous portion may be positioned relatively adjacent to (and facing) fluid inlet 112. In other embodiments, wall 121 may be substantially sintered and/or porous, such that the plurality of pores and/or passages 123 are formed between the outer surface of wall 121 and the inner surface of wall 121 along an entire length of wall 121. Each of the plurality of passages 123 may be sized, shaped, and otherwise configured such that agent 102 is inhibited from passing through passages 123 and between the inner and outer surfaces of wall 121. In further embodiments, two or more portions of wall 121 may be sintered and/or porous.

Passages 123 may be further configured to permit fluid received from fluid inlet 112 to flow through wall 121 to agitate agent 102 received in second funnel 120, as described in further detail below. The plurality of passages 123 may have sizes ranging from between approximately 40 microns and 150 microns (e.g., 100 microns). By way of illustrative example, particle sizes of agent 102 may range from approximately 200 microns to 600 microns (e.g., 320 microns to 400 microns). The plurality of passages 123 of wall 121 may cause fluid flowing through second funnel 120 to enter channel 122 at a wide variety of vectors, including angles, velocities, and/or pressures at the same time. The fluid exiting wall 121 may have a turbulent flow pattern (e.g., a radial pattern). The varying vectors with which fluid enters channel 122 may cause agent 102 within channel 122 to become fluidized. The turbulent flow of fluid (which may result in fluidization, such as a liquid sand effect, of agent 102) may aid in guiding an agitated agent 102 through outlet 150, and may prevent or minimize clogging of agent 102 within enclosure 104. Fluidization of agent 102 may assist in breaking up agglomerates of agent 102 prior to delivery through outlet 150.

Still referring to FIG. 2, tubing 116 may be coupled to second funnel 120 at distal end 128, such that tubing 116 may be in fluid communication with center opening 124. Tubing 116 may be coupled to second funnel 120 via various suitable mechanisms, including, but not limited to, an adhesive, a frictional fit, complementary ridges and/or grooves, and more. Tubing 116 may define outlet 150 of valve assembly 100, and may be in fluid communication with catheter 36 (see FIG. 1). Accordingly, the agitated agent 102 and fluid received within second funnel 120 may be received through tubing 116 (via center opening 124) and delivered to the patient via catheter 36.

Figure 5A:
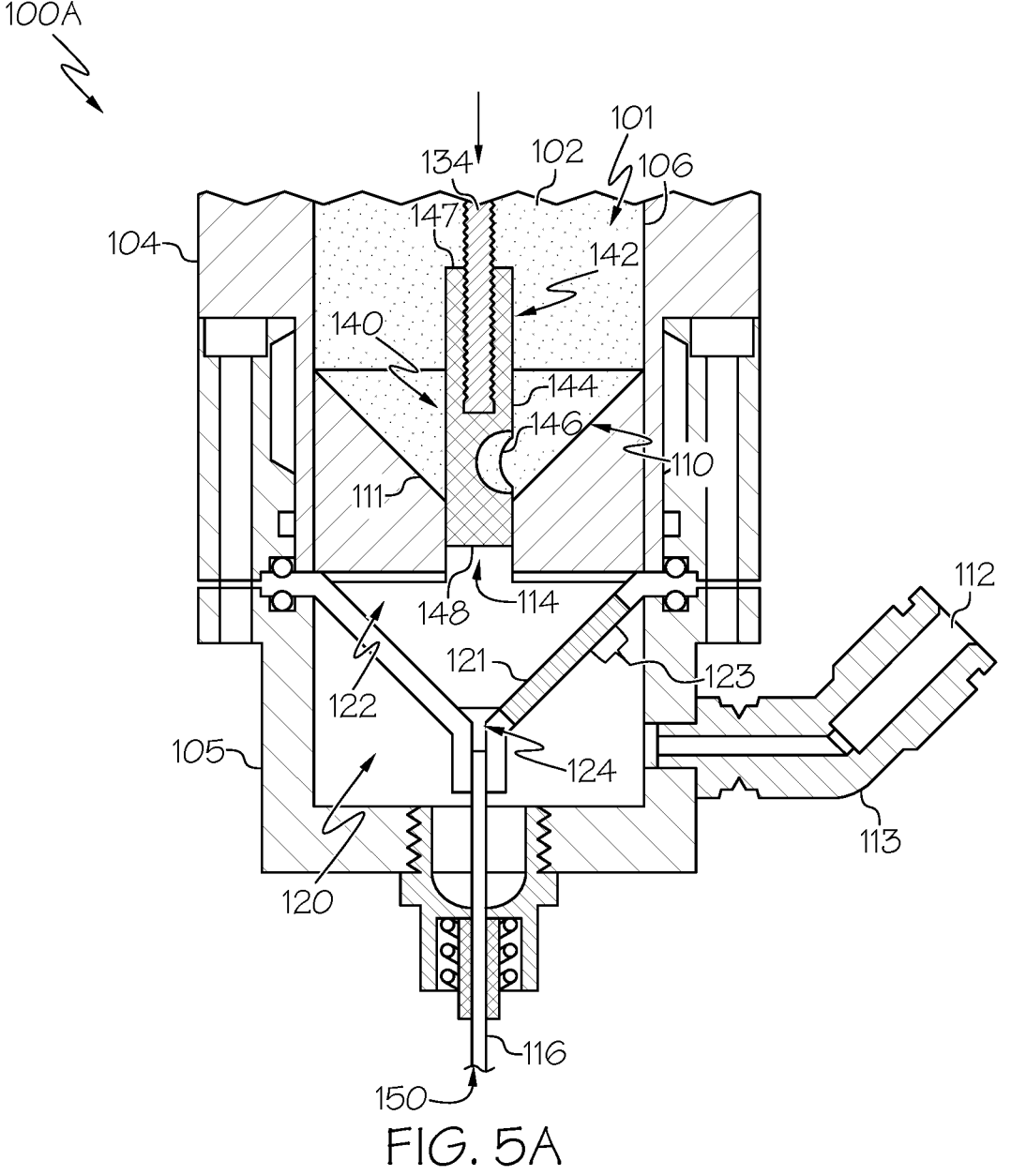
FIG. 5A shows a first actuation position of the valve assembly of FIG. 2 according to some embodiments.
Figure 5B:
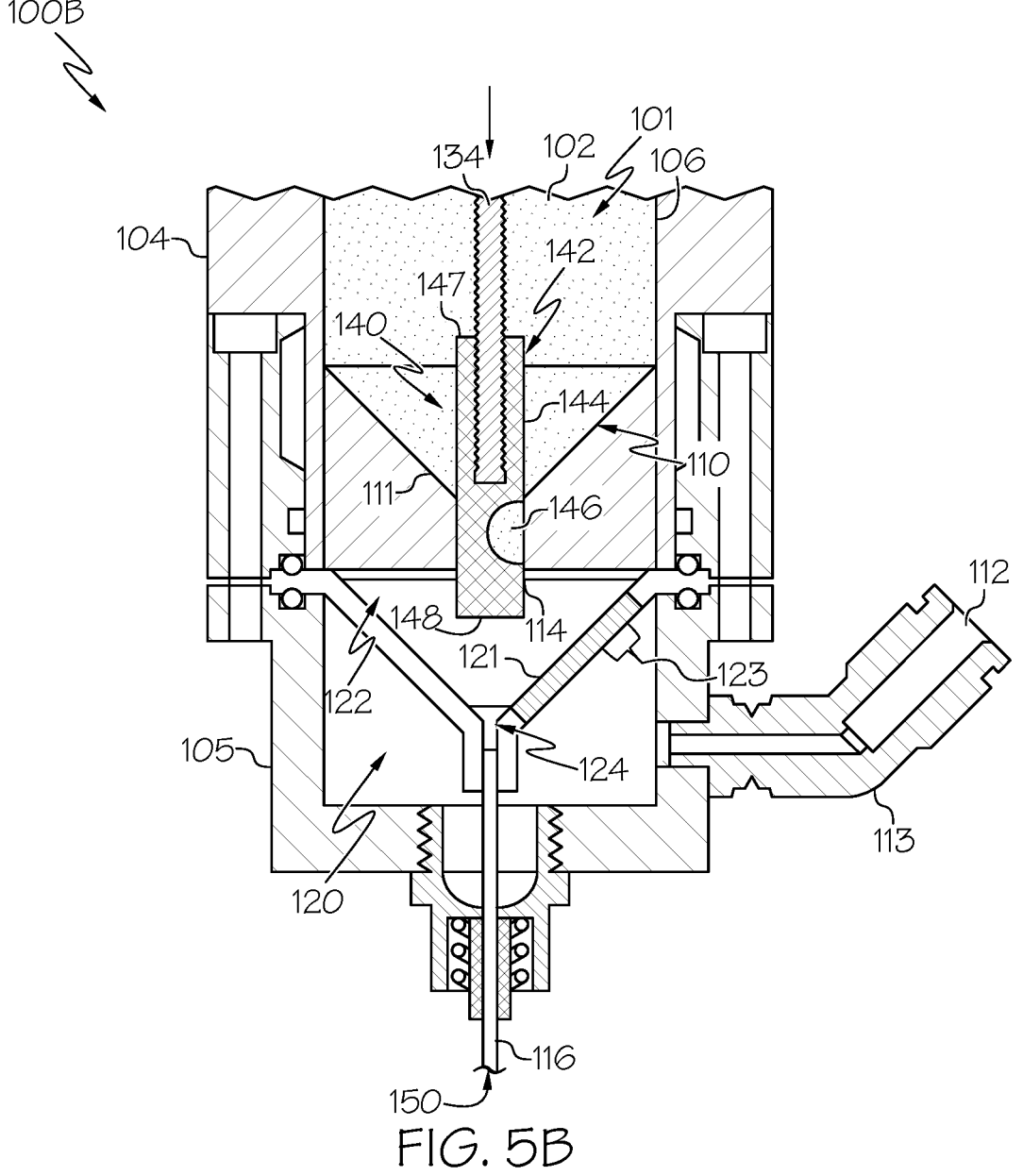
FIG. 5B shows a second actuation position of the valve assembly of FIG. 2 according to some embodiments.
Figure 5C:
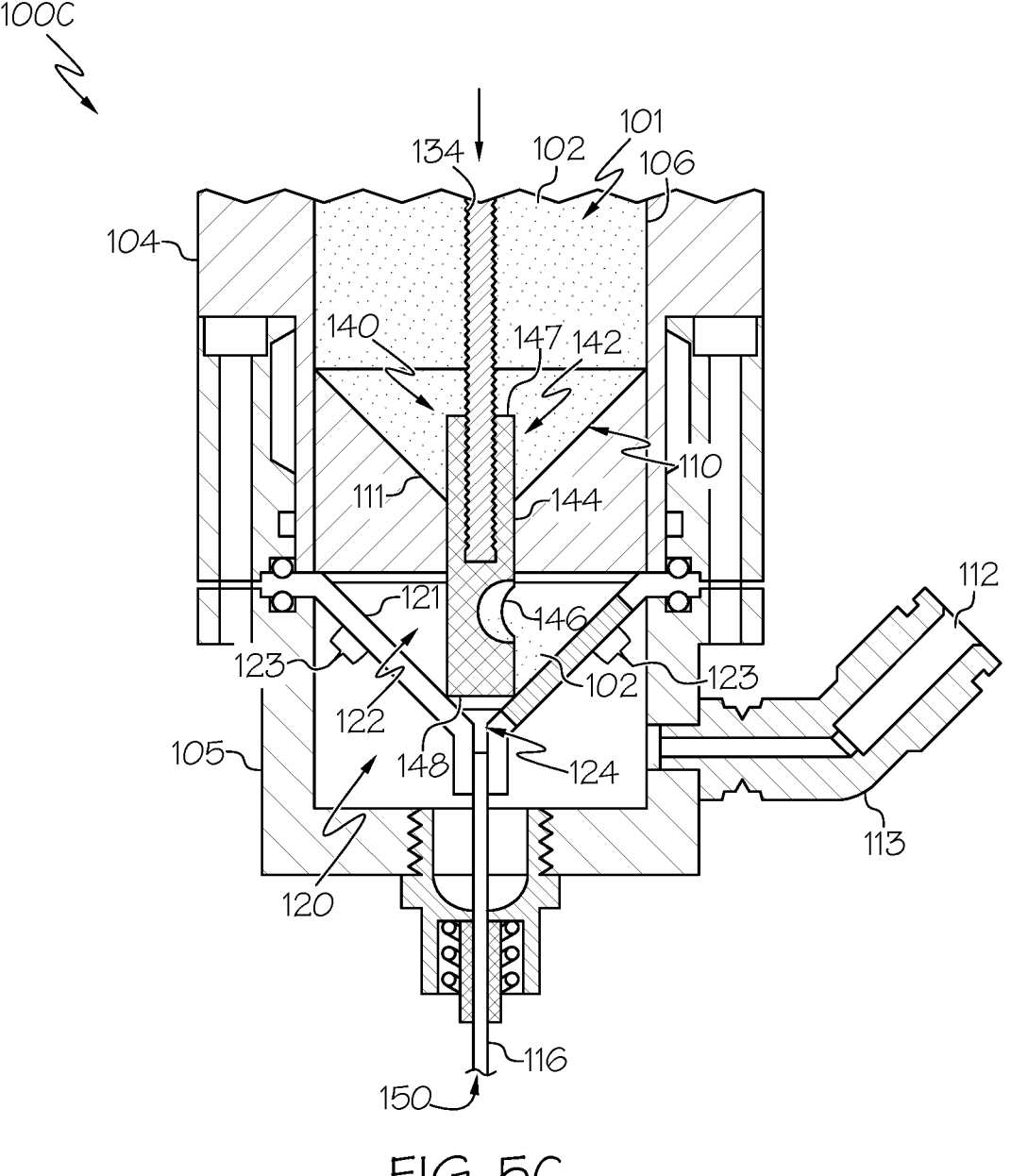
FIG. 5C shows a third actuation position of the valve assembly of FIG. 2 according to some embodiments.

In some embodiments, valve assembly 100 may include a pneumatic system 132 that is configured to transition valve assembly 100 between one or more corresponding configurations (see FIGS. 5A-5C). In the example, pneumatic system 132 may include a movable piston rod 134 and a movable piston 140, with movable piston rod 134 coupled to movable piston 140. For example, in some embodiments, movable piston 140 may include an internal threaded portion, and movable piston rod 134 may include an external threaded portion that is configured to be threadably coupled with the internal threaded portion of movable piston 140.

As described in detail herein, movable piston 140 may be configured to selectively deliver a predetermined volume of agent 102 from housing 106 to outlet 150, and particularly from first funnel 110 to second funnel 120. Pneumatic system 132 may be actuated to move movable piston rod 134 and movable piston 140 between one or more positions relative to enclosure 104, housing 106, and/or funnels 110, 120, thereby transitioning valve assembly 100 between the corresponding configurations.

Alternatively or additionally, in some embodiments, pneumatic system 132 may include a valve and/or a flow restrictor (not shown) disposed within delivery device 10, such as between the pressurized fluid source and enclosure 104. For example, the flow restrictor may be positioned within and/or in-line with fluid inlet 112, and may be configured to provide a pressure differential between cavity 101 of housing 106 (i.e., the first inlet region) and channel 122 (i.e., the second outlet region). In other words, the flow restrictor may be configured to control a flow rate and/or pressure of the fluid entering enclosure 104 from the pressurized fluid source.

Pneumatic system 132 may further include a slidable member 133 disposed within enclosure 104, and at least one biasing mechanism 136 that is configured to urge slidable member 133 in a proximal (upward) direction relative to enclosure 104. Slidable member 133 may be disposed within enclosure 104 and outside of housing 106 that stores agent 102. Slidable member 133 may be coupled to mechanical connection 130 at a proximal (upper) end of slidable member 133, and to movable piston rod 134 at a distal (lower) end of slidable member 133. Accordingly, slidable member 133 may be configured to cause a corresponding movement of movable piston rod 134 in response to movement of mechanical connection 130. In some embodiments, slidable member 133 may include an internal threaded portion, and movable piston rod 134 may include an external threaded portion that is configured to be threadably coupled with the internal threaded portion of slidable member 133.

Still referring to FIG. 2, biasing mechanism 136 may include a spring that is positioned between a distal surface of slidable member 133 and an internal surface 103 of enclosure 104. Biasing mechanism 136 may be configured to bias slidable member 133, and thereby movable piston 140 to a first position (see FIG. 5A). Pneumatic system 132 may be configured to compress biasing mechanism 136 in response to activation of actuation mechanism 30, and corresponding movement of mechanical connection 130 and slidable member 133, to move movable piston rod 134 and movable piston 140 distally (downward) relative to enclosure 104, such as to a second position (see FIG. 5B).

Movable piston 140 may be further configured to prevent agent 102 from flowing freely into channel 122 when valve assembly 100 is in one or more particular configurations, while allowing agent 102 to flow into channel 122 when valve assembly 100 is in another configuration. Although valve assembly 100 is shown and described herein as having a pneumatic system, it should be appreciated that various other suitable systems and/or devices may be utilized to provide a corresponding movement of movable piston 140 relative to enclosure 104 (e.g., hydraulic systems, mechanical linkages, actuators, etc.).

Figures 3, 4:
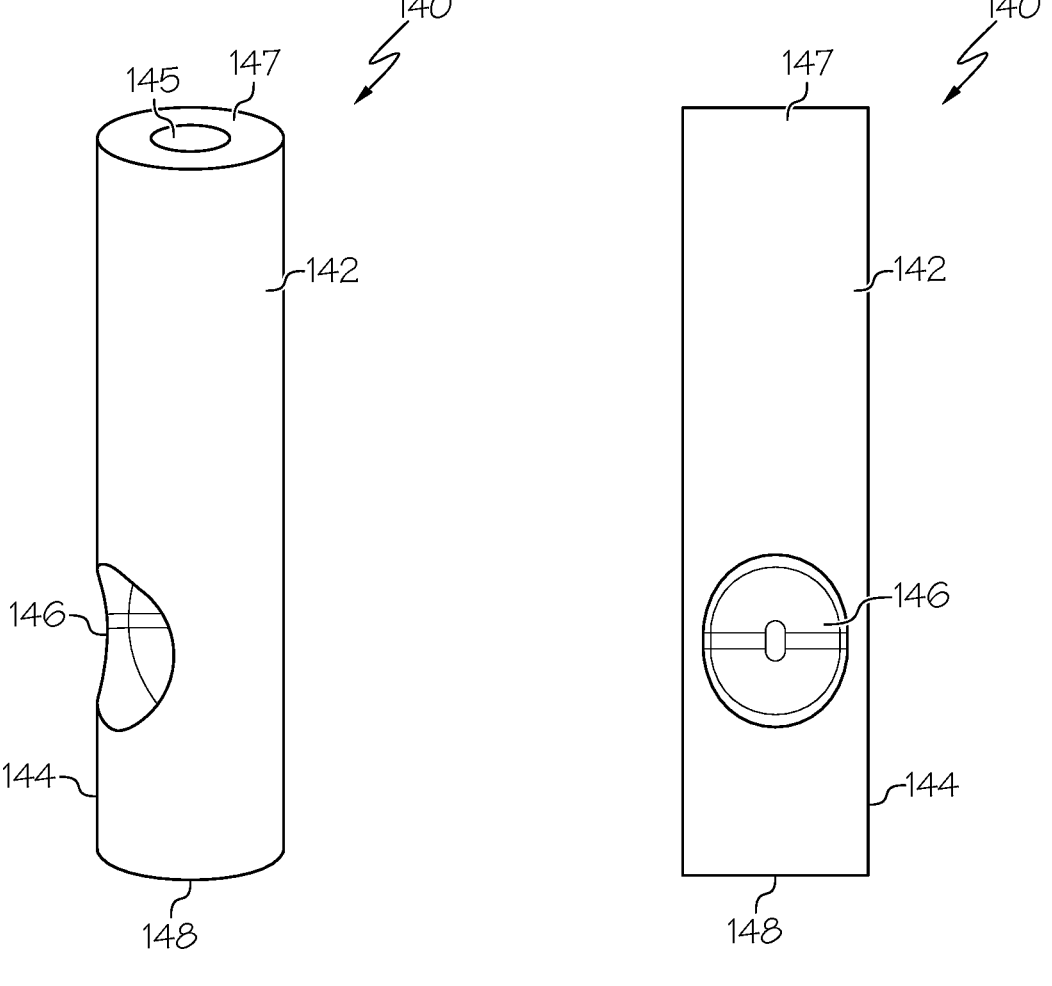
FIG. 3 shows a perspective view of a piston of the valve assembly of FIG. 2 according to some embodiments.
FIG. 4 shows a front view of the piston of FIG. 3 according to some embodiments.

Referring to FIGS. 3 and 4, movable piston 140 may include a shaft 142 having a sidewall 144. In the example, shaft 142 may have a generally cylindrical shape, and may have a longitudinal length defined between a proximal end 147 and a distal end 148. In other examples, shaft 142 may have various other suitable sizes and/or shapes, such as, an elongate body having a shape other than a cylinder. For example, shaft 142 may be in the form of a rectangular prism, a triangular prism, a pentagonal prism, and more. Movable piston 140 may include an opening 145 on shaft 142 at proximal end 147. Opening 145 may be sized and shaped to receive movable piston rod 134. In other words, movable piston 140 may be coupled to movable piston rod 134 along proximal end 147. As described herein, movable piston 140 may be configured to move (e.g., translate, rotate, etc.) relative to enclosure 104, housing 106, and/or funnels 110, 120 in response to a corresponding movement of movable piston rod 134.

Movable piston 140 may further include one or more chambers 146 defined along an exterior surface of shaft 142, such as along sidewall 144. In the example, movable piston 140 includes at least one chamber 146 positioned along sidewall 144 adjacent to distal end 148. In other examples, chamber 146 may be positioned along various other suitable locations along sidewall 144, such as adjacent to proximal end 147. Chamber 146 may define an open cavity that is sized, shaped, and otherwise configured to receive at least a portion of agent 102 therein from housing 106. In some embodiments, chamber 146 may be sized to receive a predetermined volume of agent 102, which may be chosen based on the amount of agent 102 to be delivered during a procedure. Accordingly, the cross-sectional dimension of chamber 146 may correspond to the predetermined volume of agent 102 being delivered. In some embodiments, chamber 146 may have a generally hemispherical shape. In other embodiments, chamber 146 may have various other suitable shapes adequate to hold a volume of agent 102.

Movable piston 140 may be configured to prevent agent 102 from flowing directly into channel 122 from first funnel 110 by sealing enclosure 104 at an intermediary region between first funnel 110 and second funnel 120. Stated differently, movable piston 140 may be configured to form a seal with at least a portion of housing 106 between first funnel 110 and second funnel 120, thereby controlling a delivery of agent 102 from the first (inlet) region of cavity 101 to the second (outlet) region of channel 122. Distal end 148 of movable piston 140 may be sized, shaped, and otherwise configured to fit snugly into track 114. In some embodiments, movable piston 140 has a cross-sectional profile that is substantially similar to a diameter of track 114 such that agent 102 is inhibited from flowing through track 114 when movable piston 140 is received therein. By preventing inadvertent delivery and/or leakage of agent 102 into channel 122, valve assembly 100 may be configured to inhibit delivery system 10 from clogging, thereby improving the efficiency of the device.

In exemplary use, as shown in FIGS. 5A-5C, movable piston 140 may be moved to various positions relative to enclosure 104, housing 106, and/or funnels 110, 120 to deliver a predetermined volume of agent 102 from the first (inlet) region in enclosure 104 to the second (outlet) region in channel 122.

For example, referring specifically to FIG. 5A, when valve assembly 100 is in a first actuation position 100A, movable piston 140 may be located in a first position within enclosure 104 such that chamber 146 is disposed within housing 106 and/or first funnel 110. In this instance, chamber 146 may be in fluid communication with cavity 101 (the first (inlet) region), such that movable piston 140 may be configured to receive agent 102 within chamber 146. Agent 102 may flow into chamber 146, thereby filling chamber 146 with a predefined volume of agent 102 that corresponds to a cross-sectional dimension of chamber 146. In other words, the volume of agent 102 received within chamber 146 may be predetermined and controlled based on a size and/or shape of chamber 146. It should be understood that chamber 146 may not be in fluid communication with channel 122 (the second (outlet) region) when movable piston 140 is in the first position relative to enclosure 104.

Referring now to FIG. 5B, a user may activate actuation mechanism 30 to transition valve assembly 100 from the first actuated position (FIG. 5A) to a second actuated position (FIG. 5B) to move agent 102 from enclosure 104 (and particularly first funnel 110) to channel 122 (and particularly second funnel 120). For example, activating actuation mechanism 30 may move movable piston rod 134 relative to enclosure 104, housing 106, and funnels 110, 120 via corresponding movements of pneumatic system 132. In particular, slidable member 133 may move distally, thereby compressing biasing mechanism 136, to cause a distal axial movement of movable piston rod 134. With movable piston rod 134 coupled to proximal end 147 of movable piston 140, distal axial movement of movable piston rod 134 may provide for a corresponding distal axial movement of movable piston 140 from the first position (FIG. 5A) to a second position (FIG. 5B).

Referring to FIG. 5B, with valve assembly 100 in the second actuation position 100B, chamber 146 may be positioned in an intermediary region of enclosure 104 that is not in fluid communication with cavity 101 (the first (inlet) region) or channel 122 (the second (outlet) region). In the example, the intermediary region may be positioned within track 114 between first funnel 110 and channel 122. As described above, a cross-sectional dimension and/or circumference of movable piston 140 may be substantially equal to a diameter of track 114 such that an inner wall defining track 114 may abut against an exterior surface of shaft 142 along sidewall 144, thereby effectively sealing agent 102 within chamber 146. Stated differently, an inner wall of track 114 may form a closed cavity with chamber 146 when valve assembly 100 is in the second actuated position.

Movable piston 140 may be configured to inhibit a release and/or leakage of agent 102 from chamber 146 into channel 122 when movable piston 140 is in the second position and chamber 146 forms the closed cavity. Preventing a premature leakage of agent 102 may ensure that the full volume of agent 102 within chamber 146 is delivered to channel 122 at a controlled rate. In some embodiments, the closed cavity formed by chamber 146 and the inner wall of track 114 has a hemispherical shape; however, the closed cavity may also be formed in any other shape, depending on the corresponding shape of chamber 146.

Referring now to FIG. 5C, a user may activate actuation mechanism 30 to transition valve assembly 100 from the third actuated position (FIG. 5B) to a third actuation position 100C to movable piston 140 to a third position and deliver agent 102 to channel 122. In particular, slidable member 133 may move further distally relative to enclosure 104, thereby compressing biasing mechanism 136 to a further extent (relative to an extent when valve assembly 100 is in the second actuation position 100B of FIG. 5B). Movement of slidable member 133 may cause further distal axial movement of movable piston rod 134 and movable piston 140 coupled thereto from the second position (FIG. 5B) to the third position (FIG. 5C).

In the third actuation position 100C, movable piston 140 may be positioned such that chamber 146 is in fluid communication with channel 122 (the second (outlet) region) and not in fluid communication with cavity 101 (the first (inlet) region). Movable piston 140 may be configured to release agent 102 into channel 122. Pressurized fluid from the pressurized fluid source may be permitted to flow through fluid inlet 112 and into lower cap 105, such as in response to an activation of actuation mechanism 30. The fluid from fluid inlet 112 may pass through wall 121, such as via the plurality of passages 123 of second funnel 120.

The fluid may flow into channel 122 to agitate agent 102 received within second funnel 120. Upon agitating agent 102 within channel 122, second funnel 120 may be configured to guide a mixture of the agitated agent 102 and pressurized fluid into tubing 116 via center opening 124, and out of outlet 150 of valve assembly 100. In other words, the fluid may mix with agent 102 within channel 122, and the mixture of the fluid and agent 102 may simultaneously exit valve assembly 100 via tubing 116. As only a predetermined amount of agent 102 is delivered per each actuation of delivery system 10, valve assembly 100 may allow for greater control over the amount of agent 102 delivered to a treatment site. Controlling the amount of agent delivered to the treatment site may improve a treatment of the patient.

Following delivery of agent 102 to the treatment site within the patient, movable piston 140 may be transitioned from the third position (FIG. 5C) to the first position (FIG. 5A), thereby returning valve assembly 100 to the first actuation position 100A. In this instance, channel 122 is devoid of any agent 102 for delivery through outlet 150, and the agent 102 stored in housing 106 is fluidly decoupled from outlet 150 by movable piston 140. Fluid may continue to flow from fluid inlet 112 through outlet 150, as described above, such as to purge any remaining materials and/or agent 102 maintained in tubing 116 and/or catheter 36 (FIG. 1) prior to a subsequent delivery.

If continuous delivery of agent 102 to a treatment site is desired, actuation mechanism 30 may be activated multiple times to provide controlled delivery of agent 102 to the treatment site within the patient. In some embodiments, activation mechanism 30 may be actuated in predetermined intervals, such as between about 1 second to about 5 seconds. It should be appreciated that such exemplary intervals are merely provided for illustrative purposes; such that the predetermined intervals may be longer than 5 seconds and/or shorter than 1 second without departing from a scope of this disclosure. In some embodiments, the predetermined interval may be at least partially determined based on a medical procedure.

During a release of the pressurized fluid into valve assembly 100 via fluid inlet 112, enclosure 104 may become pressurized. Aspects of delivery system 10 may facilitate depressurization of enclosure 104, such as while movable piston 140 is in the first position (FIG. 5A). Were agent 102 permitted to flow out of outlet 150 during depressurization, instances of agent 102 clogging delivery device 10 may occur. However, second funnel 120 and movable piston 140 may be configured to allow enclosure 104 to depressurize housing 106 and/or cavity 101 without agent 102 being drawn out of outlet 150 when movable piston 140 is in the first position (FIG. 5A) and/or the second position (FIG. 5B). Fluid may flow out of outlet 150 without a flow of agent

102 due to movable piston 140 inhibiting fluid communication between cavity 101 (storing agent 102) and outlet 150.

In some embodiments, valve assembly 100 may include a release valve (not shown), which may provide a mechanism for depressurizing enclosure 104. For example, the release valve may be particularly helpful in circumstances in which an increase in pressure requires an emergency release (e.g., during a procedure). The release valve may also provide a mechanism for depressurizing enclosure 104 during the ordinary course of a procedure. The release valve may be used in addition to or in alternative to the depressurizing mechanics described above. As merely an example, a relief pressure may be approximately 60 pounds per square inch gauge (PSIG).

While principles of this disclosure are described herein with reference to illustrative examples for particular applications, it should be understood that the disclosure is not limited thereto. Those having ordinary skill in the art and access to the teachings provided herein will recognize additional modifications, applications, and substitution of equivalents all fall within the scope of the examples described herein. Accordingly, the invention is not to be considered as limited by the foregoing description.

I claim:

1. A valve assembly for a medical device, comprising:
a piston configured to move relative to an enclosure of the medical device, the enclosure including a first region that is in fluid communication with an agent, and a second region including a porous funnel that is in fluid communication with a source of fluid, the piston including a chamber disposed on a sidewall of the piston, wherein the chamber is configured to receive the agent;
wherein the piston is configured to move to a first position relative to the enclosure with the chamber in fluid communication with the first region and not in fluid communication with the second region, such that the agent is received within the chamber; and
wherein the piston is configured to move to a second position relative to the enclosure with the chamber in fluid communication with the second region and not in fluid communication with the first region, such that the fluid received in the second region passes through the porous funnel to mix with the agent received in the chamber, thereby controlling delivery of the agent and the fluid from the medical device.

2. The valve assembly of claim 1, wherein the chamber comprises a closed cavity within the sidewall of the piston.

3. The valve assembly of claim 2, wherein the closed cavity has a hemispherical-shape.

4. The valve assembly of claim 1, wherein the piston is configured to move to a third position relative to the enclosure, wherein in the third position, the piston is transitioned to an intermediary region disposed between the first region and the second region, and wherein the intermediary region is not in fluid communication with either of the first region or the second region.

5. The valve assembly of claim 4, wherein the intermediary region is configured to seal the chamber when the piston is in the third position.

6. The valve assembly of claim 1, wherein the piston is coupled to an actuation mechanism of the medical device, the actuation mechanism is configured to move the piston relative to the enclosure for delivering the agent from the first region to the second region.

7. The valve assembly of claim 6, wherein the actuation mechanism comprises a pneumatic system, the pneumatic system comprising a piston rod and a spring.

8. The valve assembly of claim 7, wherein a proximal end of the piston is coupled to the piston rod.

9. The valve assembly of claim 6, wherein the piston is configured to be biased to the first position with the chamber received within the first region.

10. The valve assembly of claim 1, wherein the chamber is sized to define a volume that corresponds to a predetermined volume of the agent.

11. The valve assembly of claim 1, wherein the enclosure includes the porous funnel positioned within the second region, and the piston is configured to release the agent onto an interior surface of the porous funnel when in the second position.

12. The valve assembly of claim 11, wherein the porous funnel is in fluid communication with the source of fluid via a plurality of passages formed between the interior surface and an exterior surface of the porous funnel, and the plurality of passages extend along a length of the porous funnel such that the fluid received in the second region passes through the plurality of passages of the porous funnel for mixing with the agent.

13. The valve assembly of claim 12, wherein the porous funnel is configured to deliver the agent and the fluid to a delivery conduit of the medical device that is in fluid communication with the second region when the agent and the fluid are mixed along the porous funnel.

14. The valve assembly of claim 1, further comprising an outlet coupled to the second region.

15. The valve assembly of claim 14, further comprising a catheter coupled to the outlet, wherein the agent is released into the catheter via the outlet.

16. A device for delivering an agent, comprising:
a pressurized fluid source configured to store a pressurized fluid;
an enclosure configured to store the agent, the enclosure including an inlet region in fluid communication with the agent and an outlet region having a porous funnel that is in fluid communication with the pressurized fluid source; and
a valving assembly disposed within the enclosure, the valving assembly including a piston having a chamber disposed along a sidewall of the piston, wherein the piston is configured to move between a first position and a second position relative to the enclosure to selectively guide the agent from the inlet region to the outlet region;

wherein, in the first position, the chamber is positioned within the inlet region such that the piston is configured to receive the agent in the chamber; and
wherein, in the second position, the chamber is positioned within the outlet region such that the piston is configured to release the agent from the chamber to mix with the pressurized fluid received from the pressurized fluid source and passing through the porous funnel.

17. The device of claim 16, wherein the piston is configured to move to a third position relative to the enclosure;
wherein, in the first position, the piston is fully disposed within the inlet region such that the chamber is in fluid communication with the inlet region,
wherein, in the third position, the piston is positioned within an intermediary region disposed between the inlet region and the outlet region such that the chamber is not in fluid communication with the agent in the inlet region and the pressurized fluid in the outlet region; and
wherein, in the second position, the piston is positioned within the outlet region such that the chamber is in fluid communication with the outlet region.

18. The device of claim 17, wherein the chamber is configured to receive a volume of the agent when the piston is in the first position.

19. The device of claim 18, wherein the chamber is configured to release the volume of the agent when the piston is in the second position.

20. A method of delivering an agent from a medical device, the method comprising:
moving a piston to a first region of an enclosure of the medical device, the first region is in fluid communication with a source of the agent such that a chamber disposed on a sidewall of the piston receives a volume of the agent when the piston is in the first region;
moving the piston to a second region of the enclosure, thereby releasing the volume of the agent received in the chamber into the second region, wherein the second region is in fluid communication with a source of fluid and the enclosure includes a porous funnel within the second region;
releasing fluid into the second region from the source of fluid through the porous funnel, thereby mixing the volume of the agent with the fluid within the second region; and
delivering a mixture of the volume of the agent and the fluid from the second region through an outlet of the medical device that is in fluid communication with the second region.

* * * * *